US006831169B2

(12) United States Patent
Pachuk et al.

(10) Patent No.: US 6,831,169 B2
(45) Date of Patent: Dec. 14, 2004

(54) HEPATITIS C VIRUS VACCINE

(75) Inventors: Catherine J. Pachuk, Lansdowne, PA (US); Jack Wands, Waban, MA (US); Takaji Wakita, Winchester, MA (US); Vincent R. Zurawski, Jr., Westtown, PA (US); Leslie R. Coney, Rosemont, PA (US)

(73) Assignee: The General Hospital Corporation, Charlestown, MA (US)

( * ) Notice: Subject to any disclaimer, the term of this patent is extended or adjusted under 35 U.S.C. 154(b) by 0 days.

(21) Appl. No.: 09/788,934

(22) Filed: May 1, 2001

(65) Prior Publication Data

US 2002/0161218 A1 Oct. 31, 2002

Related U.S. Application Data

(63) Continuation of application No. 08/869,380, filed on Jun. 5, 1997, now Pat. No. 6,235,888, which is a continuation of application No. 08/318,248, filed on Oct. 5, 1994, now abandoned.

(51) Int. Cl.$^7$ ........................... C12H 15/11; C07H 21/04
(52) U.S. Cl. .................... 536/23.72; 536/23.1; 536/24.1
(58) Field of Search ............................ 536/23.1, 23.72, 536/24.1; 514/44; 424/93.1; 435/320.1

(56) References Cited

U.S. PATENT DOCUMENTS

| | | | |
|---|---|---|---|
| 5,196,194 A | 3/1993 | Rutter et al. | 424/189.1 |
| 5,204,096 A | 4/1993 | Neurath et al. | 424/189.1 |
| 5,589,466 A | 12/1996 | Felgner et al. | 514/44 |
| 5,593,972 A | 1/1997 | Weiner et al. | 514/44 |
| 5,739,118 A | 4/1998 | Carrano et al. | 514/44 |
| 6,235,888 B1 * | 5/2001 | Pachuk et al. | |

FOREIGN PATENT DOCUMENTS

| | | |
|---|---|---|
| CA | 2055149 | 5/1992 |
| EP | 0278940 | 8/1988 |
| JP | 6-92996 | 4/1994 |
| WO | WO 90/11089 | 10/1990 |
| WO | WO 93/15193 | 8/1993 |
| WO | WO 93/15207 | 8/1993 |
| WO | WO 94/16737 | 8/1994 |
| WO | WO 96/05315 | 2/1996 |

OTHER PUBLICATIONS

Gumucio Gene transfer as a new mode of vaccination: imlications for HCV 1993: 18:696–702.*
Yoshikawa et al. Chimeric hepatitis B virus core particles with parts or copies of the hepatitis C virus core protein Octn 1993 p. 6064–6070, No. 10.*
Tsopanomichaloun et al. detection of hepatitis C virus in sera and genotyping according to the 5' non–coding region 1171–1174 1997.*
Takeuchi et al. Nucleotide sequence of core and envelope genes of the hepatitis C virus genome derived directly fromn human healthy carriers vol. 18, No. 15.*
Tokushige et al. Expresison and Immune response to hepatitis C Virus Core DNA–Based Vaccine constructs pp. 14–20 Jul. 1996.*
Fukushi, 1994, Biochem Biophysical Res. Comm., vol. 199, pp. 425–432.*
Kumar, 1992, J. Genral Virol., vol. 73, pp. 1521–1525.*
Wang Jun. 1993, J. Virol., vol. 67, pp. 3338–3334.*
Yoshikawa 1992, J. Immunogical Methods, vol. 148, pp. 143–150.*
Abe et al., Genomic characterization and mutation rate of hepatitis C virus isolated from a patient who contracted hepatitis during an epidemic of non–A, non–B hepatitis in Japan, Journal of General Virology, 1992, pp. 2725–2729.
Alter, M. et al., "The Natural History of Community–Acquired Hepatitis C in the United States", N. Eng. J. of Medicine, 1992, 327 (27) 1899–1905.
Barry, M. et al., "Production of Monoclonal Antibodies by Genetic Immunization", BioTechniques, 1994, 16(4), 616, 618–19.
Bartenschlager, R. et al., "Nonstructural Protein 3 of the Hepatitis C Virus Encodes a Serine–Type Proteinase Required for Cleavage at the NS3/4 and NS4/5 Junctions", J. of Virol., 1993, 67, 3835–3844.
Blum, H. et al., "Hepatitis B Virus X Protein is not Central to the Viral Life Cycle in Vitro", J. of Virol., 1992, 66, 123–127.
Blum, H. et al., "Persistence of Hepatitis B Viral DNA After Serological Recovery from Hepatitis B Virus Infection", Hepatology, 1991, 14(1), 56–63.
Botarelli, P. et al., "T–Lymphocyte Response to Hepatitis C Virus in Different Clinical Courses of Infection", Gastroenterology, 1993, 104, 580–587.
Bukh, J et al., "Sequence Analysis of the the Core Gene of 14 Hepatitis C Virus Genotypes", PNAS USA, 1994, 91, 8239–8234.
Bukh, J. et al., "Sequence Analysis of the 5' Noncoding Region of Hepatitis C Virus", PNAS USA, 1992, 89, 4942–4946.
Cerny et al., Intl. Symp Viral Hepatitis Liver Dis., 1993, 83 (abstr).
Chen. H.–S. Et al., "The Woodchuck Hepatitis Virus X Gene is Important for Establishment of Virus Infection in Woodchuck", J. Virology, 1993, 67(3), 1218–1226.
Chiba, J. et al., "Serodiagnosis of Hepatis C Virus (HCV) Infection with an HCV Core Protein Molecularly Expressed by a Recombinant Baculovirus", PNAS USA, 1991, 88, 4641–4645.

(List continued on next page.)

Primary Examiner—Michael C. Wilson
(74) Attorney, Agent, or Firm—Woodcock Washburn LLP (57) ABSTRACT

Nucleic acid molecule that comprise an incomplete hepatitis C viral genome are provided. Pharmaceutical compositions that contain nucleic acid molecules comprising an incomplete hepatitis C viral genome including a nucleotide sequence encoding a complete hepatitis C core protein operably linked to regulatory elements functional in human cells are provided. Methods of immunizing individuals susceptible to or infected by hepatitis C virus comprising the step of administering such pharmaceutical compositions are provided.

9 Claims, 1 Drawing Sheet

OTHER PUBLICATIONS

Chisari, F. et al., "Molecular Pathogenesis of Hepatocellular Carcinoma in Hepatitis B Virus Transgenic Mice", Cell, 1989, 59, 1145–1156.

Chisari, F. et al., "Structural and Pathological Effects of Synthesis of Hepatitis B Virus Large Envelope Polypeptide in Transgenic Mice", PNAS USA, 1987, 84, 6909–6913.

Choo, Q–L. Et al., "Genetic Organization and Diversity of the Hepatitis C Virus", PNAS USA, 1991, 88, 2451–2455.

Colombo, M.. et al., "Prevalence of Antibodies to Hepatitis C Virus in Italian Patients with Hepatocellular Carcinoma", The Lancet, Oct. 28, 1989, 1006–1008.

Cox, G. et al., "Bovine Herpes virus 1: Immune Responses in Mice and Cattle Injected with Plasmid DNA", J. Virology, 1993, 67 (9), 5664, 5667.

Davis, H. et al., "DNA–based Immunization Induces Continuous Secretion of Hepatitis B Surface Antigen and High Levels of Circulating Antibody", Human Molecular Genetics, 1993, 2 (11), 1847–1851.

Farci, P. et al., "Lack of Protective Immunity Against Reinfection with Hepatitis C Virus", Science, 1992, 258, 135–140.

Farci et al., "Immunity elicited by hepatitis C virus", Clinical and Experimental Rheumatology, Nov. 1995, 13 (Supp. 13).

Ferrari, C. et al., "T–cell Response to Structural and Nonstructural Hepatitis C Virus Antigens in Persistent and Self–limited Hepatitis C Virus Infections", Hepatology, 1994, 19(2), 286–295.

Fukushi, S., et al., "complete 5' noncoding region is necessary for the efficient internal initiation of hepatitis C virus RNA," *Biochemical & Biophysical Res. Commun.,* 1994, 199, 425–432.

Fynan, E.F. et al., "Use of DNA Encoding Influenza Hemagglutinin as an Avian Influenza Vaccine", DNA and Cell Biology, 1993, 12(9), 785–789.

Ganem, D. and Varmus, "The Molecular Biology of the Hepatitis B Viruses", Ann. Rev. Biochem., 1987, 56, 651–693.

Grakoui, A. et al., "Characterization of the Hepatitis C Virus–Encoded Serine Proteinase: Determination of Proteinase–Dependent Polyprotein Cleavage Sites", J. of Virol., 1993, 67, 2823–2843.

Guidotti, L. et al., "Intracellular Inactivation of the Hepatitis B Virus by Cytotoxic T Lymphocytes", Immunity, 1996, 4, 25–36.

Guidotti, L. et al., "Cytotoxic T Lymphocytes Inhibit Hepatitis B Virus Gene Expression by a Noncytolytic Mechanism in Transgenic Mice", PNS USA, 1994, 91, 3764–3768.

Han, J.H. et al., "Characterization of the Terminal Regions of Hepatitis C Viral RNA: Identification of Conserved Sequences in the 5' Untranslated Region and Poly(A) Tails at the 3' End", PNAS USA, 1991, 88, 1711–1715.

Heinz, F.X., "Comparative Molecular Biology of Flaviviruses and Hepatitis C Virus", Arch. Virol., 1992, 4, 163–171.

Hijikata, M. et al., "Gene Mapping of the Putative Structural Region of the Hepatitis C Virus Genome in in vitro Processing Analysis", PNAS USA, 1991, 88, 5547–5551.

Hosein, B. et al., "Improved Serodiagnosis of Hepatitis C Virus Infection with Synthetic Peptide Antigen from Capsid Protein". PSAS USA. 1991, 88, 3647–3651.

Houghton, M. et al., "Molecular Biology of the Hepatitis C Viruse: Implications for Diagnosis, Development and Control of Viral Disease", Hepatology, 1991, 14, 381–388.

Hsu, H. et al., "Characterization of Hepatitis C Virus Structural Proteins with a recombinant Baculovirus Expression System", Hepatology, 1993, 17, 763–771.

Inchauspe, G. et al., "Genomic Structure of the Human Prototype Strain H of Hepatitis C Virus:Comparison with American and Japanese Isolates", PNAS USA, 1991, 88, 10292–10296.

Itoh et al., "A Synthetic Peptide Vaccine Involving the Product of the Pre–S(2) region of Hepatitis B Virus DNA: Protective Efficacy in Chimpanzees", Proc. Nat. Acad. Sci., 1986, 83, 9174–9178.

Katayama, T., et al., "Improved Serodiagnosis of Non–A, Non–B Hepatitis by an Assay Detecting Antibody to Hepatitis C Virus Core Antigen", Hepatology, 1992, 15, 391–394.

Kato, N. et al., "Characterization of Hypervariable Regions in the Putative Envelope Protein Hepatitis C Virus", Biochem. And Biophys. Res. Comm., 1992, 189(1), 119–127.

Kato, N. et al., "Molecular Cloning of the Human Hepatitis C Virus Genome from Japanese Patients with Non–A, Non–B Hepatitis", PNAS USA, 1990, 87, 9524–9528.

Kita, H. et al., "HLA B44–restricted Cytotoxic T Lymphocytes Recognizing and Epitope on Hepatitis C Virus Nucleocapsid Protein", Hepatology, 1993, 18, 1039–1044.

Korba, B. et al., "Hepatocellular Carcinoma in Woodchuck Hepatitis Virus–Infected Woodchucks: Presence of Viral DNA in Tumor Tissue from Chronic Carriers and Animals Serologically Recovered from Acute Infections", Hepatology, 1989, 9(3), 461–470.

Korba, B. et al.,. "Natural History of Woodchuck Hepatitis Virus Infections During the Course of Experimental Viral Infection:Molecular Virologic Features of the Liver and Lymphoid Tissues", J. Virology, 1989, 63 (3), 1360–1370.

Koziel, M. et al., "Hepatitis C Virus (HCV) –Specific Cytotoxic T Lymphocytes Recognize Epitopes in the Core and Envelope Proteins of HCV", J. Virology, 1993, 67 (12), 7522–7532.

Koziel, M. et al., "Intrahepatic Cytotoxic t Lymphoctyes Specific for Hepatitis C Virus in Persons with Chronic Hepatitis", The J. of Immunology, 1992, 149, 3339–3344.

Kumar, O., "Cloning and sequencing of the structural region and expression of putative core gene of hepatitis C virus from a British case of chronic sporadio hepatitis," *J. General Virology,* 1992, 73, 1521–1525.

Manthorpe, M. et al., "Gene Therapy by Intramuscular Injection of Plasmid DNA Studies on Firefly Luciferase Gene Expression in Mice", Human Gene Therapy, 1993, 4, 419–431.

Marquardt, O. et al., "Cell Type Specific Expression of Pre S1 Antigen and Secretion of Hepatitis B Virus Surface Antigen", *Arch. Virol.,* 1987, 98, 249–256.

Martell, M. et al., "Hepatitis C Virus (HCV) Circulates as a Population of Different but Closely Related Genomes: Quasispecies Nature of HCV Genome Distribution", *J. Virology,* 1992, 66(5), 3225–3229.

Montgomery, D. et al., "Heterologous and Homologous Protection Against Influenza A by DNA Vaccination: Optimization of DNA Vectors", *DNA and Cell Biology,* 1993, 12(9), 777–783.

Moriyama, T. et al. "Immunobiology and Pathogenesis of Hepatocellular Injury in Hepatitis B Virus Transgenic Mice", *Science,* 1990, 24, 361–364.

Nasoff, M. et al., "Identification of an immunodominant epitope within the capsid protein of hepatitis C virus", *PNAS USA,* 1991, 88, 5462–5466.

Okamoto et al., "Full Length Sequence of a Hepatitis C Virus Genome Having Poor Homology to Reported Isolates; Comparative Study of Four Distinct Genotype", Virology, 188,. 1992–pp. 331–341.

Okamoto et al., "Nucleotide Sequence of the genomic RNA of hepatitis C virus isolated from a human carrier; comparison with reported isolates for conserved and divergent regions", J. of General Virology, 1991, vol. 72, pp. 2697–2704.

Okamoto, H. et al., "Antobodies Against Synthetic Oligopeptides Deduced from the Putative Core Gene for the Diagnosis of Hepatitis C Virus Infection", Hepatology, 1992, 15, 180–186.

Okamoto, H. et al., "Typing Hepatitis B Virus by Homology in Nucleotide Sequence Comparison of Surface Antigen Sybtypes", J. Gen. Virol., 1988, 69, 2575–2583.

Okamoto, H., et al., "The entire nucleotide sequence and classification of a hepatitis C virus isolate of a novel genotype from an indonesian patient with chronic liver disease," J. General Virology, 1994, 75, 629–635.

Persing, D. et al., "Inhibition of Secretion of Hepatitis B Surface Antigen by a Related Presurface Polypeptide", Science, 1986, 234, 1388–1391.

Ross, G. et al., "Gene Therapy in the United States: A Five-Year Status Report", Human Gene Therapy, Sep. 10, 1996, 7, 1781–1790.

Saito, I. Et al., "Hepatitis C Virus Infection is Associated with the Development of Hepatocelllular Carcinoma", PNAS USA, 1990, 87, 6547–6549.

Santolini, E. et al, "Biosynthesis and Biochemical Properties of the Hepatitis C Virus Core Protein", J. Virology, 1994, 68 (6), 3631–3641.

Schupper, H. et al., "Peripheral–blood Mononuclear Cell Responses to Recombinant Hepatitis C Virus Antigens in Patients with Chronic Hepatitis C", Hepatology, 1993, 18, 1055–1060.

Selby, M. et al., "Expression, Identification and Subcellular Localization of the Proteins Encoded by the Hepatitis C Viral Genome", J. Gen. Virol., 1993, 74, 1103–1113.

Schödel, F. et al., "The Biology of Avian Hepatitis B Viruses", Chapter 3 in "Molecular Biology of the Hepatitis B Virus", 1991, vol. 3, CRC Press, Boca Raton, FL, pp. 53–80.

Schek, N. et al., "The Hepadnaviral X Protein", Chap. 9 in "Molecular Biology of the Hepatitis B Virus", 1991, vol. 3, CRC Press, Boca Raton, FL, pp. 181–192.

Shih, C.–M. Et al., "Suppression of Hepatitis B Virus Expression and Replication by Hepatitis C Virus Core Protein in HuH–7 Cells" J. of Virol., 1993, 67 (10), 5823–5832.

Shirai, M. et al., "An Epitope in Hepatitis C Virus Core Region Recognized by Cytotoxic T Cells in Mice and Humans", J. Virology, 1994, 68 (5), 3332–3342.

Simmonds, P. et al., "Classification of Hepatitis C Virus into Six Major Genotypes and a Series of Subtypes by Phylogenetic Analysis of the NS–5 region", J. Gen. Virol., 1993, 74, 2391–2399.

Simonetti, R. G. et al., "Hepatitis C Virus Infection as a Risk Factor for Hepatocellular Carcinoma in Patients with Cirrhosis", Annals of Internal Medicine, 1992, 116 (2), 97–102.

Takamizawa, A. et al., "Structure and Organization of the Hepatitis C Virus Genome Isolated from Human Carriers", J. of Virol.., 1991, 65, 1105–1113.

Tanaka et al., "Molecular cloning of hepatitis C virus genome from a single Japanese carrier; sequence variation within the same individual and among infected individuals", Virus Research, 23, 1992, pp. 39–53.

Tang, D. et al., "Genetic Immunization is a Simple Method for Eliciting an Immune Response", Nature, 1992, 356, 152–154.

Tokushige et al., "Expression and Immune Response to Hepatitis C Virus Core DNA–Based Vaccine Constructs", Hepatology, 1996, 24(1), 14–20.

Tsopanomichalou et al, "Detection of hepatitis C virus in sera and genotyping according to the 5' non–coding region", Oncology Reports, vol. 4, pp. 1171–1174 (1997).

Tsukuma H. et al., "Risk Factors for Hepatocellular Carcinoma Among Patients with Chronic Liver Disease", N. Eng. J. of Med., 1993, 328 (25), 1797–1801.

Ulmer, J.B., et al., "Gene transfer as a new mode of vaccination: implications for HCV," Hepatology Elsewhere, 1993, 18, 696–702.

Ulmer, J. et al., "Heterologous Protection Against Influenz0056a by Injection of DNA Encoding a Viral Protein", Science, 1993, 259, 1745–1749.

Valenzuela, P. eta l., "The Nucleotide Sequence of the Hepatitis B Viral Genome and the Identification of the Major Viral Genes, in Animal Virus Genetics", Fields, B. et al., eds., Acadmic Press, NY, 1980, pp. 57–70.

Verma et al., "Gene therapy—promises, problems and prospects", Nature, Sep. 18, 1997, vol. 389, pp. 239–342 (Sep. 18, 1997).

Wakita, T. et al., "Specific Inhibition of Hepatitis C. Virus Expression by Antisense Oligodeoxynucleotides", J. Biol. Chem., 1994, 269, 14205–14210.

Wang, Y. et al., "Prevalence, Genotypes and Isolate (HC–C2) of Hepatitis C Virus in Chinese Patients with Liver Disease", J. of Medical Virology 1993, 40, 254–260.

Wang, B. et al., "DNA Inoculation Induces Neutralizing Immune Responses Against Human Immunodeficiency Virus Type 1 in Mice and Nonhuman Primates", DNA and Cell Biology, 1993, 12 (9), 799–805.

Wang, C. et al., "Translation of Human Hepatitis C Virus RNA in Cultured Cells is Mediates by an Internal Ribosome–Binding Mechanism", J. Virology, 1993, 67 (6), 3338–3344.

Wang, B. et al., "Gene Inoculation Generates Immune Responses Against Human Immunodeficiency Virus Type 1", PNAS USA, 1993, 90, 4156–4160.

Wells, D. et al., "Improved gene transfer by direct plasmid injection associated with regeneration in mouse skeletal muscle", FEBS, 1993, 332, 179–182.

Weiner, A. et al., "Variable and Hypervariable Domains are Found in the Regions of HCV Corresponding to the Flavivirus Envelope and NSI Proteins and the Pestivirus Envelope Glycoproteins", Virology, 1991, 180, 842–848.

Weiner, A. et al., "Evidence for Immune Selection of Hepatitis C Virus (HCV) Putative Envelope Glycoprotein Variants' Potential Role in Chronic HCV Infections", PNAS USA, 1992, 89, 3468–3472.

Wolff, J. et al, "Direct Gene Transfer into Mouse Muscle in Vivo", Science, 1990, 247, 1465–1468.

Wolff, J. et al., "Long–term Persistence of Plasmid DNA and Foreign Gene Expression in Mouse Muscle", Human Molecular Genetics, 1992, 1 (6) 363–369.

Xiang, Z. et al., "Vaccination with a Plasmid Vector Carrying the Rabies Virus Glycoprotein Gene Induces Protective Immunity against Rabies Virus", Virology, 1994, 199, 1132–140.

Yoshikawa et al., "Chimeric Hepatitis B Virus Core Particles with Parts or Copies of the Hepatitis C Virus Core Protein", J. Virology, 1993, 67 (10) 6064–6070.

* cited by examiner

HEPATITIS C VIRUS VACCINE

CROSS REFERENCE TO RELATED APPLICATIONS

This application is a continuation of U.S. Ser. No. 08/869,380, filed Jun. 5, 1997, now U.S. Pat. No. 6,235,888 which is a continuation of U.S. Ser. No. 08/318,248, filed Oct. 5, 1994, now abandoned, each of which is incorporated herein in its entirety.

ACKNOWLEDGMENT OF GOVERNMENT RIGHTS

This invention was made with Government support under grants CA-35711 and AA-0186 awarded by the National Institutes of Health. The Government has certain rights in this invention.

FIELD OF THE INVENTION

The present invention relates to gene constructs which are useful as anti-hepatitis C virus vaccine components in genetic immunization protocols, to methods of protecting individuals against hepatitis C virus infection and to methods of treating individuals suffering from hepatitis C virus infection.

BACKGROUND OF THE INVENTION

Hepatitis C virus (HCV), the major etiologic agent of transfusion acquired non-A, non-B hepatitis is responsible for approximately 150,000 new cases of acute viral hepatitis annually in the United States (Greenberger, N.J., 1983, "New Approaches for Hepatitis C", *Contemporary Internal Medicine* Feb:64). Approximately half of these infections progress to a chronic infection that can be associated with cirrhosis and/or hepatocellular carcinoma.

HCV is an enveloped, positive stranded RNA virus which has recently been classified as a separate genus within the Flavivirus family (Heinz, F. X., 1992 "Comparative Molecular Biology of Flaviviruses and Hepatitis C Virus", *Arch. Virol.* (Suppl.) 4:163). The viral genome is approximately 9,500 nucleotides in length and contains one long open reading frame that encodes a precursor polyprotein of 330 Kd. Individual HCV polypeptides are produced by proteolytic processing of the precursor polypeptide. This proteolysis is catalyzed by a combination of both cellular and viral encoded proteases.

In addition to the translated region, the HCV genome also contains both a 5' untranslated region (5' UTR) and a 3' untranslated region (3' UTR). The 5' UTR represents the most highly conserved sequence among all HCV isolates reported to date, and thus has been postulated to contain important regulatory elements for replication and/or translation of HCV RNAs. The 5' UTR also contains several small open reading frames (orf) but there is presently no evidence to suggest that these orf sequences are actually translated.

Development of a vaccine strategy for HCV is complicated not only by the significant heterogeneity among HCV isolates, but also by the mixture of heterogeneous genomes within an isolate (Martell, M. et al., 1992 "Hepatitis C Virus (HCV) Circulates as a Population of Different But Closely Related Genomes: Quasispecies Nature of HCV Genome Distribution", *J. Virol.* 66:3225). In addition, the virus contains a highly variable envelope region.

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

PCT patent application PCT/US90/01348 discloses sequence information of clones of the HCV genome, amino acid sequences of HCV viral proteins and methods of making and using such compositions including anti-HCV vaccines comprising HCV proteins and peptides derived therefrom.

U.S. Ser. No. 08/008,342 filed Jan. 26, 1993, now abandoned, U.S. Ser. No. 08/029,336 filed Mar. 11, 1993, now abandoned U.S. Ser. No. 08/125,012 filed Sep. 21, 1993, now U.S. Pat. No. 5,593,972, PCT patent application Ser. No. PCT/US94/00899 filed Jan. 26, 1994, and U.S. Ser. No. 08/221,579 filed Apr. 1, 1994 now U.S. Pat. No. 5,739,118 each contains descriptions of genetic immunization protocols. Vaccines against HCV are disclosed in each.

There remains a need for vaccines useful to protect individuals against hepatitis C virus infection. There remains a need for methods of protecting individuals against hepatitis C virus infection.

SUMMARY OF THE INVENTION

The present invention relates to nucleic acid molecules comprising an incomplete hepatitis C viral genome including SEQ ID NO:1.

The present invention relates to nucleic acid molecules comprising an incomplete hepatitis C viral genome including a nucleotide sequence that encodes the HCV core protein and at least the last 9 nucleotides of the 5' untranslated region.

The present invention relates to pharmaceutical compositions that comprise a nucleic acid molecule having an incomplete hepatitis C viral genome and at least the coding sequences of SEQ ID NO:1 operably linked to regulatory elements functional in human cells.

The present invention relates to pharmaceutical compositions that comprise a nucleic acid molecule having an incomplete hepatitis C viral genome including a nucleotide sequence that encodes the HCV core protein and at least the last 9 nucleotides of the 5' untranslated region operably linked to regulatory elements functional in human cells.

The present invention relates to a method of immunizing an individual susceptible to or infected by hepatitis C virus comprising the step of administering to the individual, an amount of plasmid pHCV2-1 or plasmid pHCV4-2 effective to induce a protective or therapeutic immune response against hepatitis C virus infection.

DETAILED DESCRIPTION OF THE INVENTION

According to the present invention, compositions and methods are provided which prophylactically and/or therapeutically immunize an individual against HCV infection. Genetic material constituting an incomplete hepatitis C viral genome but which encodes HCV core protein is administered to the individual. The protein encoded by the gene construct is expressed by the individual's cells and serves as an immunogenic target against which an anti-HCV immune response is elicited. The resulting immune response is broad based; in addition to a humoral immune response, both arms of the cellular immune response are elicited. The methods of the present invention are useful for conferring prophylactic and therapeutic immunity. Thus, a method of immunizing includes both methods of protecting an individual from HCV challenge as well as methods of treating an individual suffering from HCV infection.

As used herein, the term "incomplete hepatitis C viral genome" is meant to refer to a nucleic acid molecule that does not contain the complete coding sequence for the HCV polyprotein which is encoded by the HCV viral genome. Incorporation of an incomplete HCV genome into a cell does not constitute introduction of sufficient genetic information for the production of infectious virus.

As used herein the term "HCV core protein" is meant to refer to the HCV core protein having the amino acid sequence disclosed in SEQ ID NO:1 and SEQ ID NO:2 which is the amino acid sequence of the HCV core protein of a specific HCV isolate. In addition, the term HCV core protein is meant to refer to corresponding HCV core proteins from other HCV isolates. Those having ordinary skill in the art can readily identify the HCV core protein from other HCV isolates.

The HCV core protein has been observed to exist as two distinct forms, the anchored core protein and the virion core protein. During HCV translation, a precursor polypeptide is translated and subsequently processed by cellular proteases and viral proteases to yield the individual viral polypeptides. A cellular signal peptidase is believed to cleave at a site which separates the portion of the polyprotein that becomes the core protein from the portion that becomes the envelope protein, thereby releasing anchored core protein from the envelope protein. Anchored core protein, which is associated with the endoplasmic reticulum, is further processed to mature virion core. Anchored core protein differs from virion core in that it contains an extra 18 amino acids at the C terminus. Virtually no anchored core is found on viral particles.

As used herein, the term "gene construct" is meant to refer to a nucleic acid molecule that comprises a nucleotide sequence which encodes the HCV core protein including initiation and termination signals operably linked to regulatory elements including a promoter and polyadenylation signal capable of directing expression in the cells of the vaccinated individual. In some embodiments, the gene construct further comprises at least a fragment of the HCV 5' UTR.

As used herein, the term "genetic vaccine" refers to a pharmaceutical preparation that comprises a gene construct. Genetic vaccines include pharmaceutical preparations useful to invoke a prophylactic and/or therapeutic immune response.

According to the present invention, gene constructs are introduced into the cells of an individual where it is expressed, thus producing the HCV core protein. The regulatory elements of the gene constructs of the invention are capable of directing expression in human cells. The regulatory elements include a promoter and a polyadenylation signal. In addition, other elements, such as a Kozak region, may also be included in the gene construct.

When taken up by a cell, the gene constructs of the invention may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the gene construct as a linear minichromosome including a centromere, telomeres and an origin of replication.

According to the present invention, the gene construct includes coding sequences which encode the HCV core protein. In some preferred embodiments, the gene construct encodes an anchored form of the HCV core protein. Anchored core protein is preferred in some embodiments for the following reasons. First, it is believed to be desirable to correctly compartmentalize the core protein to the endoplasmic reticulum where the core protein is first found in naturally infected cells. If a protein is incorrectly compartmentalized, there is a risk of lowering total expression of that protein due to degradation or poisoning of the cell. Further, since a cellular protease is thought to cleave anchored core to virion core, both species may be present in cells expressing the anchored form. If there are differences in the antigenicity between the two species, a broader immune response against core is potentially generated by expressing the anchored form of core protein. Moreover, the extra 18 amino acids in the anchored core may contain either antibody epitopes or cytotoxic T cell epitopes or both. Expression of the anchored form provides the presence of these regions which may broaden the immune response to core protein.

In some preferred embodiments, the gene construct encodes an HCV core protein which consists of the amino acid sequence of SEQ ID NO:1 and SEQ ID NO:2. In some preferred embodiments, the gene construct comprises the coding sequence in SEQ ID NO:1.

In some preferred embodiments, the gene construct includes at least a fragment of the HCV 5' UTR including the last 9 nucleotides of the HCV 5' UTR. As used herein, the term "the last 9 nucleotides of the HCV 5' UTR" is meant to refer to the 9 most 3' nucleotides of the 5' UTR. That is, the 9 nucleotides of the 5' UTR that immediately precede the coding sequence. The last 9 nucleotides of the HCV 5' UTR of a preferred embodiment is shown as SEQ ID NO:3.

In some embodiments, the fragment of the 5' UTR that includes the last 9 nucleotides of the HCV 5' UTR comprises the last 25 nucleotides of the HCV 5' UTR. In some embodiments, the fragment of the 5' UTR that includes the last 9 nucleotides of the HCV 5' UTR comprises the last 50 nucleotides of the HCV 5' UTR. In some embodiments, the fragment of the 5' UTR that includes the last 9 nucleotides of the HCV 5' UTR comprises the last 75 nucleotides of the HCV 5' UTR. In some embodiments, the fragment of the 5' UTR that includes the last 9 nucleotides of the HCV 5' UTR comprises the last 100 nucleotides of the HCV 5' UTR. In some embodiments, the fragment of the 5' UTR that includes the last 9 nucleotides of the HCV 5' UTR comprises the last 150 nucleotides of the HCV 5' UTR. In some embodiments, the fragment of the 5' UTR that includes the last 9 nucleotides of the HCV 5' UTR comprises the last 200 nucleotides of the HCV 5' UTR. In some embodiments, the fragment of the 5' UTR that includes the last 9 nucleotides of the HCV 5' UTR comprises the last 250 nucleotides of the HCV 5'

UTR. In some embodiments, the fragment of the 5' UTR that includes the last 9 nucleotides of the HCV 5' UTR comprises the last 300 nucleotides of the HCV 5' UTR.

In some preferred embodiments, the gene construct includes the entire HCV 5' UTR. In some preferred embodiments, the gene construct includes the 9 most 3' nucleotides of the HCV 5' UTR. The entire HCV 5' UTR of a preferred embodiment is shown as SEQ ID NO:4.

In some preferred embodiments, the gene construct comprises SEQ ID NO:1.

The regulatory elements necessary for gene expression of a DNA molecule include: a promoter, an initiation codon, a stop codon, and a polyadenylation signal. In addition, enhancers are often required for gene expression. It is necessary that these elements be operable linked to the sequence that encodes the HCV core protein and that the regulatory elements are operably in the individual to whom they are administered.

Initiation codons and stop codon are generally considered to be part of a nucleotide sequence that encodes the core protein.

Promoters and polyadenylation signals used must be functional within the cells of the individual. In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego, Cailf.), referred to as the SV40 polyadenylation signal, is used.

In addition to the regulatory elements required for gene expression, other elements may also be included in a gene construct. Such additional elements include enhancers. The enhancer may be selected from the group including but not limited to: human Actin, human Myosin, human Hemoglobin, human muscle creatine and viral enhancers such as those from CMV, RSV and EBV.

Gene constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

Figure 1:
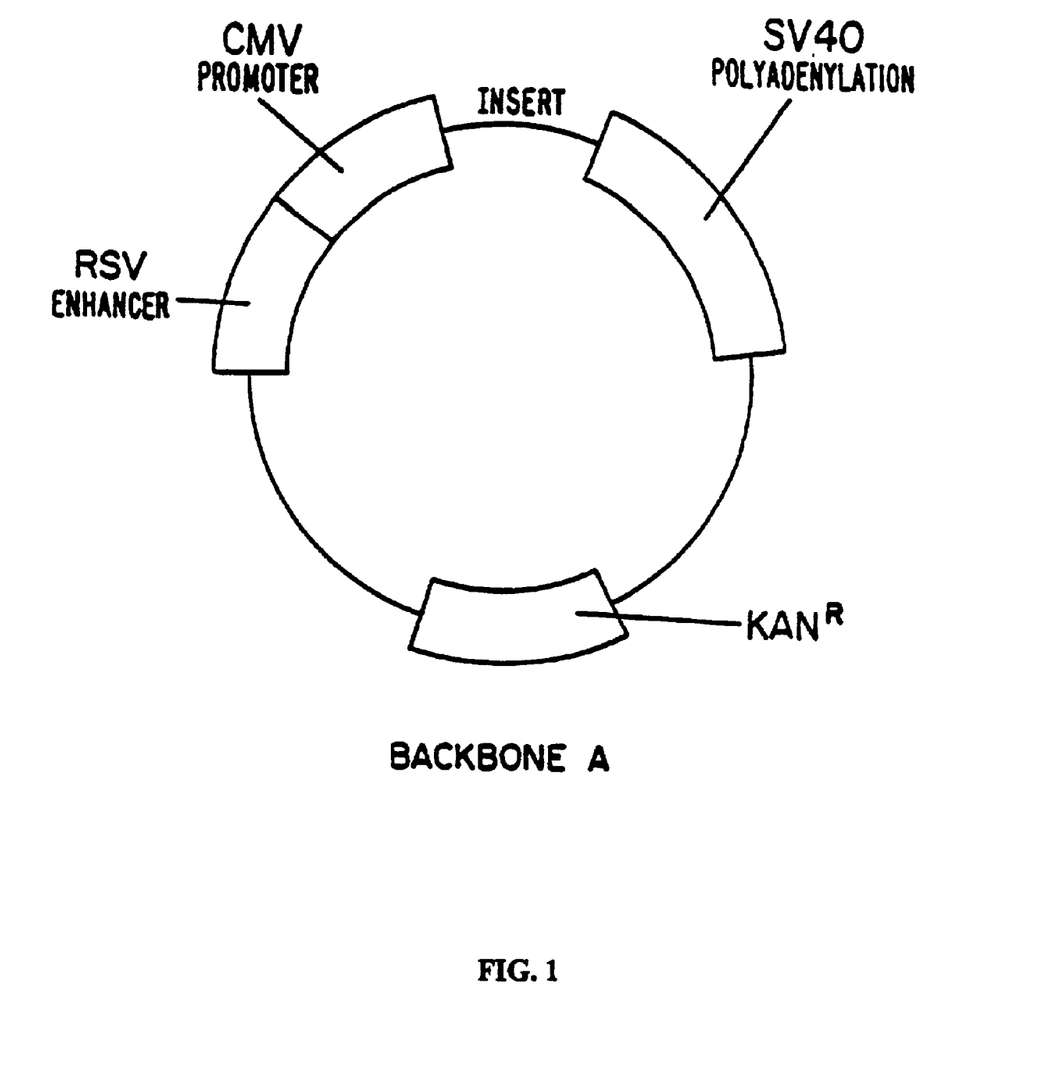
FIG. 1 shows a diagram of the plasmid vector into which HCV coding sequence is inserted to produce plasmids pHCV2-1 and pHCV4-2.

In some preferred embodiments, the vector used is selected from those described in FIG. 1. In some embodiments, nucleotides 342 to 923 of SEQ ID NO:1 is inserted into backbone A to form plasmid pHCV2-1. In some embodiments, SEQ ID NO:1 is inserted into bac bone A to form plasmid pHCV4-2.

In plasmids pHCV2-1 and pHCV4-2, coding sequence encoding the HCV core protein is under the regulatory control of the CMV immediate early promoter and the SV40 minor polyadenylation signal. Constructs may optionally contain the SV40 origin of replication.

Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Delivery of gene constructs which encode HCV core protein can confer mucosal immunity in individuals immunized by a mode of administration in which the material is presented in tissues associated with mucosal immunity. Thus, in some examples, the gene construct is delivered by administration in the buccal cavity within the mouth of an individual.

Gene constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the gene construct is taken up by the cells, they are reimplanted into the individual. It is contemplated that otherwise non-immunogenic cells that have gene constructs incorporated therein can be implanted into the individual even if the vaccinated cells were originally taken from another individual.

According to some embodiments of the present invention, the gene construct is administered to an individual using a needleless injection device. According to some embodiments of the present invention, the gene construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

The genetic vaccines according to the present invention comprise about 1 nanogram to about 1000 micrograms of DNA. In some preferred embodiments, the vaccines contain about 10 nanograms to about 800 micrograms of DNA. In some preferred embodiments, the vaccines contain about 0.1 to about 500 micrograms of DNA. In some preferred embodiments, the vaccines contain about 1 to about 350 micrograms of DNA. In some preferred embodiments, the vaccines contain about 25 to about 250 micrograms of DNA. In some preferred embodiments, the vaccines contain about 100 micrograms DNA.

The genetic vaccines according to the present invention are formulated according to the mode of administration to be used. One having ordinary skill in the art can readily formulate a pharmaceutical composition that comprises a gene construct. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

The gene constructs of the invention may be formulated with or administered in conjunction with agents that increase uptake and/or expression of the gene construct by the cells relative to uptake and/or expression of the gene construct by the cells that occurs when the identical genetic vaccine is administered in the absence of such agents. Such agents and the protocols for administering them in conjunction with gene constructs are described in U.S. Ser. No. 08/008,342 filed Jan. 26, 1993, now abandoned, U.S. Ser. No. 08/029,336 filed Mar. 11, 1993, now abandoned, U.S. Ser. No. 08/125,012 filed Sep. 21, 1993, now U.S. Pat. No. 5,593,972, PCT patent application Ser. No. PCT/US94/00899 filed Jan. 26, 1994, and U.S. Ser. No. 08/221,579 filed Apr. 1, 1994, now U.S. Pat. No. 5,739,118 which are each incorporated herein by reference. Examples of such agents include: $CaPO_4$, DEAE dextran, anionic lipids; extracellular matrix-active enzymes; saponins; lectins; estrogenic compounds and steroidal hormones; hydroxylated lower alkyls; dimethyl sulfoxide (DMSO); urea; and benzoic acid esters anilides, amidines, urethanes and the hydrochloride salts thereof such as those of the family of local anesthetics. In addition, the gene constructs are encapsulated within/administered in conjunction with lipids/polycationic complexes.

EXAMPLES

Example 1
Design and Construction of HCV Expression Plasmids

Plasmids, pHCV2-1 and pHCV4-2, were both designed to express the anchored core protein of HCV. Anchored core, the cellular precursor to virion core, remains membrane associated by means of a hydrophobic carboxy terminus.

Each plasmid construct contains the HCV core coding region placed under the transcriptional control of the CMV promoter and the RSV enhancer element. Plasmid pHCV2-1 contains a 9 nucleotide fragment of the 5' UTR of HCV which includes the 9 most 3' nucleotides of the 5' UTR of HCV. Plasmid pHCV4-2 differs from plasmid pHCV2-1 in that it also contains the entire 5' UTR of HCV.

HCV specific sequences were amplified by Polymerase Chain Reaction (PCR) using pUC-T7-HCVTH (HCV Type 2) as a template and oligonucleotides comprises of the following sequences as PCR primers SEQ ID NO:5, SEQ ID NO:6 and SEQ ID NO:7.

The 5' PCR primers, SEQ ID NO:5 and SEQ ID NO:7 have NatI sites and the 3' PCR primer SEQ ID NO:6 has a SalI site. Three stop codons engineered into SEQ ID NO:6. SEQ ID NO:7 and SEQ ID NO:6 were used as primers to generate a PCR product which maps from position 1 to position 810 of the HCV genome and which contains the entire 5' HCV untranslated region and core coding region.

The use of SEQ ID NO:5 and SEQ ID NO:6 as primers resulted in a PCR product mapping from position 333 to position 810 of the HCV genome. This product contains the last 9 nucleotides of the HCV 5' untranslated region and the entire core coding region.

Both PCR products were digested with NatI and SalI (NED), gel purified and ligated into the NatI-SalI sites of plasmid Backbone A shown in FIG. 1 to generate pHCV4-2 and pHCV2-1.

Plasmid backbone A is 3969 base pairs in length. It contains a PBR origin of replication for replicating in *E. coli*. It also contains a kanamycin resistance gene so that the plasmid can be selected in *E. coli*. Inserts such as the HCV core gene, are cloned into a polylinker region which places the insert between and operably linked to the promoter and polyadenylation signal. Transcription of the cloned inserts is under the control of the CMV promoter and the RSV enhancer elements. A polyadenylation signal is provided by the presence of an SV40 poly A signal situated just 3' of the cloning site.

Example 2
In vitro Expression Analysis

Expression of HCV core from pHCV2-1 and pHCV4-2 was assayed in vitro in a rhabdomyosarcoma (RD) cell line. Cells were co-transfected with pHCV2-1 and a B-galactosidase reporter plasmid, pCMVB (Clonetech), pHCV4-2 and pCMVB, vector plasmid and pCMVB, or mock transfected. All analyses were conducted at 48 hrs. post-transfection. The transfection efficiency was determined by measuring the specific activity of B-galactosidase in cell lysates.

Transfected cells were analyzed by indirect immunofluorescence using either an anti-core monoclonal antibody or pooled HCV patent sera as the primary antibodies. FITC labelled anti-mouse 1gG (Sigma) and FITC labelled anti-human 1gG (Sigma) were used respectively as the secondary antibodies. Immunostaining was seen in cells that had been transfected with either pHCV2-1 or pHCV4-2 but not in cells transfected with the vector plasmid or mock transfected. Immunofluorescence in fixed cells appeared as punctate staining localized to the cytoplasm when either the monoclonal antibody or the pooled patient's sera was used as the source of primary antibody. There appeared to be no difference in the level or type of staining between pHCV2-1 and pHCV4-2 transfected cells. No staining was seen in unfixed cells indicating that the expressed core protein is probably not associated with the cell's surface membrane.

Transfected cell lysates were also analyzed by Western blot and immunoprecipitation. The presence or absence of the HCV 5' UTR seemed to have little effect upon the expression of core since pHCV2-1 and pHCV4-2 expressed equivalent amounts of core in the cell lines tested.

Example 3
DNA Inoculation

Humoral immunity in a group of six mice was assessed following a single intramuscular inoculation of 100 μg of pHCV4-2 plus 0.25% bupivacaine. All mice were shown to have seroconverted 21 days after DNA inoculation. The humoral response persisted for several months. Studies are currently underway to evaluate the effect of multiple dosing.

This HCV core DNA-based vaccine expresses high levels of core antigen in vitro and induces a strong immune response in vivo.

What is claimed is:

1. An isolated and purified nucleic acid molecule having a nucleoude sequence comprising an incomplete hepatitis C viral genome, said genome comprising a coding sequence for a hepatitis C virus core protein comprising SEQ ID NO:2 and a 5' untranslated region of hepatitis C virus.

2. The nucleic acid molecule of claim 1 wherein said coding sequence is operably linked to a promoter and polyadenylation sequence.

3. The nucleic acid molecule of claim 1 wherein said nucleic acid molecule is plasmid pHCV2-1.

4. An isolated and purified nucleic acid molecule having a nucleotide sequence encoding SEQ ID NO:2 and a 5' untranslated region of hepatitis C virus.

5. The nucleic acid molecule of claim 4, wherein said 5' untranslated region of hepatitis C virus comprises SEQ ID NO:4.

6. An isolated and purified nucleic acid molecule comprising a coding sequence and a non-coding sequence, said coding sequence consisting of a nucleotide sequence encoding the hepatitis C virus core protein wherein said hepatitis C virus core protein consists of SEQ ID NO:2.

7. The nucleic acid molecule of claim 6 further comprising a 5' untranslated region of hepatitis C virus.

8. The nucleic acid molecule of claim 7 wherein said 5' untranslated region of hepatitis C virus comprises SEQ ID NO:4.

9. The nucleic acid molecule of claim 6 wherein said coding sequence is operably linked to a promoter and polyadenylation sequence.

* * * * *

UNITED STATES PATENT AND TRADEMARK OFFICE
CERTIFICATE OF CORRECTION

PATENT NO. : 6,831,169 B2
APPLICATION NO. : 09/788934
DATED : December 14, 2004
INVENTOR(S) : Pachuk et al.

It is certified that error appears in the above-identified patent and that said Letters Patent is hereby corrected as shown below:

Title Page,
Item (56), FOREIGN PATENT DOCUMENTS:
Please insert missing reference:
--JP     6-141870     5/1994-- therefor.

Title Page,
Item (56), OTHER PUBLICATIONS:
"Gumucio Gene transfer" reference, please delete "imlications" and insert -- implications -- therefor,
"Takeuchi et al." reference, please delete "fromn" and insert -- from -- therefor.
"Bukh, J. et al." reference, please delete "of the the" and insert -- of the -- therefor.
"Chiba, J. et al." reference, please delete "Hepatis" and insert -- Hepatitis -- therefor.
"Houghton, M. et al." reference, please delete "Viruse:" and insert -- Viruses: -- therefor.
"Okamoto et al." reference, please delete "Isolates;" and insert -- Isolates: -- and please delete " Genotype", " and insert -- Genotypes", -- therefor.
"Okamoto, H. et al." reference, please delete " "Antobodies " and insert -- "Antibodies -- therefor.
"Okamoto, H. et al." reference, please delete " Sybtypes", " and insert -- Subtypes", -- therefor.
"Saito, I. Et al." reference, please delete "Hepatocelllular" and insert -- Hepatocellular -- therefor.
"Valenzuela, P." reference, please delete "eta l.," and insert -- et al., -- and please delete "Acadmic" and insert -- Academic -- therefor.

Column 6,
Line 3, please delete "bac bone" and insert -- backbone -- therefor.

UNITED STATES PATENT AND TRADEMARK OFFICE
CERTIFICATE OF CORRECTION

PATENT NO. : 6,831,169 B2
APPLICATION NO. : 09/788934
DATED : December 14, 2004
INVENTOR(S) : Pachuk et al.

It is certified that error appears in the above-identified patent and that said Letters Patent is hereby corrected as shown below:

<u>Column 13,</u>
Line 61, please delete "nucleoude" and insert -- nucleotide -- therefor.

Signed and Sealed this

Twenty-fifth Day of September, 2007

JON W. DUDAS
*Director of the United States Patent and Trademark Office*

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 923 base pairs
      (B) TYPE: nucleic acid
      (C) STRANDEDNESS: double
      (D) TOPOLOGY: linear    (ii) MOLECULE TYPE: cDNA    (ix) FEATURE:
      (A) NAME/KEY: CDS
      (B) LOCATION: 342..914

(xi) SEQUENCE DESCRIPTION: SEQ ID NO: 1:

```
GCCAGCCCCC GATTGGGGGC GACACTCCAC CATAGATCAC TCCCCTGTGA GGAACTACTG      60

TCTTCACGCA GAAAGCGTCT AGCCATGGCG TTAGTATGAG TGTCGTGCAG CCTCCAGGAC     120

CCCCCCTCCC GGGAGAGCCA TAGTGGTCTG CGGAACCGGT GAGTACACCG GAATTGCCAG     180

GACGACCGGG TCCTTTCTTG GATCAACCCG CTCAATGCCT GGAGATTTGG GCGTGCCCCC     240

GCGAGACTGC TAGCCGAGTA GTGTTGGGTC GCGAAAGGCC TTGTGGTACT GCCTGATAGG     300

GTGCTTGCGA GTGCCCCGGG AGGTCTCGTA GACCGTGCAC C ATG AGC ACG AAT         353
                                             Met Ser Thr Asn
                                               1

CCT AAA CCT CAA AGA AAA ACC AAA CGT AAC ACC AAC CGC CGC CCA CAG       401
Pro Lys Pro Gln Arg Lys Thr Lys Arg Asn Thr Asn Arg Arg Pro Gln
  5                  10                  15                  20

GAC CTC AAG TTC CCG GGC GGT GGT CAG ATC GTT GGT GGA GTT TAC CTG       449
Asp Leu Lys Phe Pro Gly Gly Gly Gln Ile Val Gly Gly Val Tyr Leu
                 25                  30                  35

TTG CCG CGC AGG GGC CCC AGG TTG GGT GTG CGC GCG ACT AGG AAG ACT       497
Leu Pro Arg Arg Gly Pro Arg Leu Gly Val Arg Ala Thr Arg Lys Thr
             40                  45                  50

TCC GAG CGG TCG CAA CCT CGT GGA AGG CGA CAA CCT ATC CCC AAG GAT       545
Ser Glu Arg Ser Gln Pro Arg Gly Arg Arg Gln Pro Ile Pro Lys Asp
         55                  60                  65

CGC CGG CCC GAG GGC AGG GCC TGG GCT CAA CCT GGG TAC CCT TGG CCC       593
Arg Arg Pro Glu Gly Arg Ala Trp Ala Gln Pro Gly Tyr Pro Trp Pro
     70                  75                  80

CTC TAT GGC AAC GAG GGC ATG GGG TGG GCA GGA TGG CTC CTG TCA CCC       641
Leu Tyr Gly Asn Glu Gly Met Gly Trp Ala Gly Trp Leu Leu Ser Pro
 85                  90                  95                 100

CGT GGC TCC CGG CCT AGT TGG GGC CCC AAT GAC CCC CGG CGT AGG TCG       689
Arg Gly Ser Arg Pro Ser Trp Gly Pro Asn Asp Pro Arg Arg Arg Ser
                105                 110                 115

CGT AAT TTG GGT AAA GTC ATC GAT ACC CTT ACA TGC GGC TTC GCC GAC       737
Arg Asn Leu Gly Lys Val Ile Asp Thr Leu Thr Cys Gly Phe Ala Asp
            120                 125                 130

CTC ATG GGG TAC ATT CCG CTC GTC GGC GCT CCC ATG GGG GGC GCT GCC       785
Leu Met Gly Tyr Ile Pro Leu Val Gly Ala Pro Met Gly Gly Ala Ala
        135                 140                 145

AGG GCC TTG GCG CAT GGC GTC CGG GTT CTG GAG GAC GGC GTG AAC TAT       833
Arg Ala Leu Ala His Gly Val Arg Val Leu Glu Asp Gly Val Asn Tyr
    150                 155                 160
```

```
GCA ACA GGG AAT CTG CCC GGT TGC TCT TTC TCT ATC TTC CTC TTG GCT      881
Ala Thr Gly Asn Leu Pro Gly Cys Ser Phe Ser Ile Phe Leu Leu Ala
165             170                 175                 180

CTG CTG TCC TGT TTG ACC ATC CCA GCT TCC GCT TAATAATAA                923
Leu Leu Ser Cys Leu Thr Ile Pro Ala Ser Ala
            185                 190
```

(2) INFORMATION FOR SEQ ID NO: 2:

(i) SEQUENCE CHARACTERISTICS:
        (A) LENGTH: 191 amino acids
        (B) TYPE: amino acid
        (D) TOPOLOGY: linear     (ii) MOLECULE TYPE: protein     (xi) SEQUENCE DESCRIPTION: SEQ ID NO: 2:

```
Met Ser Thr Asn Pro Lys Pro Gln Arg Lys Thr Lys Arg Asn Thr Asn
 1               5                  10                  15

Arg Arg Pro Gln Asp Leu Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
        50                  55                  60

Ile Pro Lys Asp Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Met
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190
```

(2) INFORMATION FOR SEQ ID NO: 3:

(i) SEQUENCE CHARACTERISTICS:
        (A) LENGTH: 9 base pairs
        (B) TYPE: nucleic acid
        (C) STRANDEDNESS: double
        (D) TOPOLOGY: linear     (ii) MOLECULE TYPE: cDNA     (xi) SEQUENCE DESCRIPTION: SEQ ID NO: 3:

```
CCGTGCACC                                                              9
```

(2) INFORMATION FOR SEQ ID NO: 4:

(i) SEQUENCE CHARACTERISTICS:
        (A) LENGTH: 341 base pairs
        (B) TYPE: nucleic acid
        (C) STRANDEDNESS: double
        (D) TOPOLOGY: linear -continued (ii) MOLECULE TYPE: cDNA (xi) SEQUENCE DESCRIPTION: SEQ ID NO: 4:

| | | | | | |
|---|---|---|---|---|---|
| GCCAGCCCCC | GATTGGGGGC | GACACTCCAC | CATAGATCAC | TCCCCTGTGA | GGAACTACTG | 60
| TCTTCACGCA | GAAAGCGTCT | AGCCATGGCG | TTAGTATGAG | TGTCGTGCAG | CCTCCAGGAC | 120
| CCCCCCTCCC | GGGAGAGCCA | TAGTGGTCTG | CGGAACCGGT | GAGTACACCG | GAATTGCCAG | 180
| GACGACCGGG | TCCTTTCTTG | GATCAACCCG | CTCAATGCCT | GGAGATTTGG | GCGTGCCCCC | 240
| GCGAGACTGC | TAGCCGAGTA | GTGTTGGGTC | GCGAAAGGCC | TTGTGGTACT | GCCTGATAGG | 300
| GTGCTTGCGA | GTGCCCCGGG | AGGTCTCGTA | GACCGTGCAC | C | | 341

(2) INFORMATION FOR SEQ ID NO: 5:

(i) SEQUENCE CHARACTERISTICS:
        (A) LENGTH: 47 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO: 5:

AAAAAGGGAA GGAAGGCGGC CGCCCGTGCA CCATGAGCAC GAATCCT    47

(2) INFORMATION FOR SEQ ID NO: 6:

(i) SEQUENCE CHARACTERISTICS:
        (A) LENGTH: 57 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO: 6:

AAAAAGGGAA GGAAGGTCGA CTTATTATTA TTAAGCGGAA GCTGGGATGG TCAAACA    57

(2) INFORMATION FOR SEQ ID NO: 7:

(i) SEQUENCE CHARACTERISTICS:
        (A) LENGTH: 47 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO: 7:

AAAAAGGGAA GGAAGGCGGC CGCGCCAGCC CCCGATTGGG GGCGACA    47